United States Patent
Mattsson et al.

(10) Patent No.: US 9,563,788 B2
(45) Date of Patent: *Feb. 7, 2017

(54) TOKENIZATION IN A CENTRALIZED TOKENIZATION ENVIRONMENT

(71) Applicant: Protegrity Corporation, George Town, Grand Cayman (KY)

(72) Inventors: Ulf Mattsson, Cos Cob, CT (US); Yigal Rozenberg, Wilton, CT (US)

(73) Assignee: Protegrity Corporation, Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 14/738,830

(22) Filed: Jun. 13, 2015

(65) Prior Publication Data

US 2015/0312246 A1    Oct. 29, 2015

Related U.S. Application Data

(63) Continuation of application No. 13/851,854, filed on Mar. 27, 2013, now Pat. No. 9,202,086.

(Continued)

(51) Int. Cl.
*G06F 21/60* (2013.01)
*G06F 21/62* (2013.01)
(Continued)

(52) U.S. Cl.
CPC ......... *G06F 21/6254* (2013.01); *G06F 17/277* (2013.01); *G06F 17/30312* (2013.01);
(Continued)

(58) Field of Classification Search
CPC  G06F 21/6245; G06F 21/6254; G06F 19/322; G06F 21/60; G06F 17/30914; G06F 17/30312; G06F 17/277; H04L 63/0823
See application file for complete search history.

(56) References Cited

U.S. PATENT DOCUMENTS 6,507,846 B1    1/2003 Consens
7,120,933 B2   10/2006 Mattsson
(Continued)

OTHER PUBLICATIONS

United States Office Action, U.S. Appl. No. 13/851,854, Mar. 2, 2015, 23 pages.

(Continued)

*Primary Examiner* — Theodore C Parsons
(74) *Attorney, Agent, or Firm* — Fenwick & West LLP (57) ABSTRACT

Data can be protected in a centralized tokenization environment. A request to tokenize sensitive data is received by an endpoint. A token for use in tokenizing the sensitive data is identified. A token certificate store is queried for a token certificate associated with the identified token. The token certificate can include a token status and use rules describing a permitted use of the token. Responsive to the token certificate store storing the queried token certificate, the endpoint tokenizes the sensitive data using the identified token if the token status indicates the token is available, and subject to the use rules included in the token certificate being satisfied. The token certificate is updated based on the tokenization of the sensitive data with the identified token and stored at the token certificate store.

21 Claims, 5 Drawing Sheets

Related U.S. Application Data (60) Provisional application No. 61/618,622, filed on Mar. 30, 2012.

(51) Int. Cl.
*G06F 19/00* (2011.01)
*H04L 29/06* (2006.01)
*G06F 17/30* (2006.01)
*G06F 17/27* (2006.01)

(52) U.S. Cl.
CPC ...... *G06F 17/30914* (2013.01); *G06F 19/322* (2013.01); *G06F 21/6245* (2013.01); *H04L 63/0823* (2013.01)

(56) References Cited

U.S. PATENT DOCUMENTS

| | | | |
|---|---|---|---|
| 7,305,707 B2 | 12/2007 | Mattsson | |
| 8,225,106 B2 | 7/2012 | Mattsson | |
| 8,683,209 B2* | 3/2014 | Li | H04L 9/321 713/168 |
| 2003/0115467 A1* | 6/2003 | Aull | H04L 63/0853 713/173 |
| 2008/0019527 A1 | 1/2008 | Youn et al. | |
| 2008/0082834 A1 | 4/2008 | Mattsson | |
| 2009/0249082 A1 | 10/2009 | Mattsson | |
| 2009/0313477 A1 | 12/2009 | Park et al. | |
| 2010/0070754 A1* | 3/2010 | Leach | H04L 63/0428 713/152 |
| 2010/0325443 A1 | 12/2010 | Mattsson | |
| 2011/0078779 A1* | 3/2011 | Liu | G06F 21/31 726/9 |
| 2011/0154467 A1* | 6/2011 | Bomar | G06F 21/335 726/9 |
| 2011/0182430 A1* | 7/2011 | Furukawa | H04L 9/0844 380/277 |
| 2011/0213807 A1 | 9/2011 | Mattsson | |
| 2011/0274273 A1 | 11/2011 | Fiske | |
| 2011/0307714 A1* | 12/2011 | Comrie | G06F 21/6209 713/189 |
| 2012/0167189 A1* | 6/2012 | Aichroth | H04L 9/006 726/7 |
| 2012/0316992 A1* | 12/2012 | Oborne | G06Q 30/06 705/26.41 |
| 2013/0103685 A1 | 4/2013 | Preneel et al. | |
| 2013/0110658 A1* | 5/2013 | Lyman | G06Q 20/20 705/18 |
| 2013/0205371 A1* | 8/2013 | Laurier | G06F 21/606 726/4 |
| 2013/0283059 A1* | 10/2013 | Sabapathy | G06F 21/6254 713/189 |

OTHER PUBLICATIONS

United States Office Action, U.S. Appl. No. 13/851,854, Sep. 11, 2014, 21 pages.

* cited by examiner

TOKENIZATION IN A CENTRALIZED TOKENIZATION ENVIRONMENT

CROSS REFERENCE TO RELATED APPLICATIONS

This application is a continuation of U.S. application Ser. No. 13/851,854, filed Mar. 27, 2013, now U.S. Pat. No. 9,202,086, which application claims the benefit of Provisional Application No. 61/618,622, filed on Mar. 30, 2012, the contents of which are incorporated herein by reference.

FIELD OF ART

This application relates generally to the field of data protection, and more specifically to the use and maintenance of token certificates in a centralized tokenization environment.

BACKGROUND

Many challenges exist in handling financial and other sensitive data, such as credit card numbers, social security numbers, bank account numbers, and the like. To prevent unauthorized access to sensitive data, steps can be taken to protect the sensitive data. Such data protection measures are required by many jurisdictions for various categories of sensitive data. The sensitive data can be encrypted during transmission or storage using an encryption algorithm and encryption key. However, encryption can be overcome/broken using a variety of hacking methods, and the use of encryption in financial systems is often subject to resource-intensive audit requirements. Data storage security measures can be implemented while the sensitive data is stored at an authorized entity, but such storage security measures generally protect against intrusion by an unauthorized entity and do not protect the sensitive data after the unauthorized entity has overridden or bypassed the storage security measures.

SUMMARY

Data can be protected in a centralized tokenization environment. A request to tokenize sensitive data is received by an endpoint. A token for use in tokenizing the sensitive data is identified. A token certificate store ("TCS") is queried for a token certificate associated with the identified token. The TCS stores a plurality of token certificates, and receives token certificates queries for a plurality of endpoints. The token certificate can include a token status and use rules describing a permitted use of the token. Responsive to the TCS storing the queried token certificate, the endpoint tokenizes the sensitive data using the identified token if the token status indicates the token is available, and subject to the use rules included in the token certificate being satisfied. The token certificate is updated based on the tokenization of the sensitive data with the identified token by the endpoint and stored at the TCS. Updating the token certificate can include changing the status of the token within the token certificate (for instance, from "available" to "checked out").

If the token status included within the queried token certificate indicates that the identified token is checked out or revoked, or if a use rule included in the token certificate is not satisfied by the requested tokenization, the endpoint can deny the tokenization request. Alternatively, the endpoint can identify a second token for use in tokenizing the sensitive data, and can query the TCS for a token certificate associated with the second identified token to ensure that the status of the second identified token is available.

If the TCS does not store the queried token certificate, the endpoint can tokenize the sensitive data with the identified token, and a token certificate associated with the identified token can be generated based on the tokenization for storage in the TCS. The endpoint can tokenize sensitive data in a "fast mode" by tokenizing the sensitive data with an identified token prior to querying the TCS for a token certificate associated with the identified token. When operating in fast mode, collisions between endpoints requesting the same token can occur, but the performance of the endpoint in tokenizing the sensitive data can be improved.

The figures depict embodiments for purposes of illustration only. One skilled in the art will readily recognize from the following description that alternative embodiments of the structures and methods illustrated herein may be employed without departing from the principles of the invention described herein.

DETAILED DESCRIPTION

Tokenization Overview

As used herein, the tokenization of data refers to the generation of tokenized data by querying one or more token tables mapping input values to tokens with one or more portions of the data, and replacing the queried portions of the data with the resulting tokens from the token tables. Tokenization can be combined with encryption for increased security, for example by encrypting sensitive data using a mathematically reversible cryptographic function (e.g., datatype-preserving encryption or DTP), a one-way non-reversible cryptographic function (e.g., a hash function with strong, secret salt), or a similar encryption before or after the tokenization of the sensitive data. Any suitable type of encryption can be used in the tokenization of data.

As used herein, the term token refers to a string of characters mapped to an input string of characters in a token table, used as a substitute for the string of characters in the creation of tokenized data. A token may have the same number of characters as the string being replaced, or can have a different number of characters. Further, the token may have characters of the same type (such as numeric, symbolic, or alphanumeric characters) as the string of characters being replaced or characters of a different type. Tokens can be randomly generated and assigned to a particular token table input value.

Any type of tokenization may be used to perform the functionalities described herein. One such type of tokenization is static lookup table ("SLT") tokenization. SLT tokenization maps each possible input values (e.g., possible character combinations of a string of characters) to a particular token. An SLT includes a first column comprising permutations of input string values, and may include every possible input string value. The second column of an SLT includes tokens, with each associated with an input string value of the first column. Each token in the second column may be unique among the tokens in the second column. Optionally, the SLT may also include one or several additional columns with additional tokens mapped to the input string values of the first column. A seed value can be used to generate an SLT, for instance by generating random numbers based on the seed value for each token in the SLT.

In some embodiments, to increase the security of tokenization, sensitive data can be tokenized two or more times using the same or additional token tables. Each successive tokenization is referred to as a "tokenization iteration" herein. For example, the first 8 digits of a 16 digit credit card number can be tokenized with an 8 digit token table to form first tokenized data, and the last 12 digits of the first tokenized data can be tokenized using a 12 digit token table to form second tokenized data. In another example, the first 4 digits of a credit card number are tokenized using a first token table, the second 4 digits are tokenized with a second token table, the third 4 digits are tokenized with a third token table, and the last 4 digits are tokenized with a fourth token table. Certain sections of the sensitive data may also be left un-tokenized; thus a first subset of the resulting tokenized data may contain portions of the sensitive data and a second subset of the tokenized data may contain a tokenized version of the sensitive data.

Dynamic token lookup table ("DLT") tokenization operates similarly to SLT tokenization, but instead of using static tables for multiple tokenizations, a new token table entry is generated each time sensitive data is tokenized. A seed value can be used to generate each DLT. In some embodiments, the sensitive data or portions of the sensitive data can be used as the seed value. DLTs can in some configurations provide a higher level of security compared to SLT, but can also require the storage and/or transmission of a large amount of data associated with each of the generated token tables. While DLT tokenization can be used to tokenize data according to the principles described herein, the remainder of the description will be limited to instances of SLT tokenization for the purposes of simplicity The security of tokenization can be further increased through the use of initialization vectors ("IVs"). An IV is a string of data used to modify sensitive data prior to tokenizing the sensitive data. Example sensitive data modification operations include performing linear or modulus addition on the IV and the sensitive data, performing logical operations on the sensitive data with the IV, encrypting the sensitive data using the IV as an encryption key, and the like. The IV can be a portion of the sensitive data. For example, for a 12-digit number, the last 4 digits can be used as an IV to modify the first 8 digits before tokenization. IVs can also be retrieved from an IV table, received from an external entity configured to provide IVs for use in tokenization, or can be generated based on, for instance, the identity of a user, the date/time of a requested tokenization operation, based on various tokenization parameters, and the like. Data modified by one or more IVs that is subsequently tokenized includes an extra layer of security—an unauthorized party that gains access to the token tables used to tokenized the modified data will be able to detokenize the tokenized data, but will be unable to de-modify the modified data without access to the IVs used to modify the data.

As used herein, "tokenization parameters" refers to the properties or characteristics of a tokenization operation. For example, tokenizing data according to tokenization parameters can refer to but is not limited to one or more of the following: the generation of token tables for use in tokenizing the data; the identity of pre-generated token tables for use in tokenizing the data; the type and number of token tables for use in tokenizing the data; the identity of one or more tokens for use in tokenizing the data; the number of tokenization iterations to perform; the type, number, and source of initialization vectors for use in modifying the data prior to tokenization; the portion of sensitive data to be tokenized; and encryption operations to perform on the data before or after tokenization. Tokenization and initialization vectors are described in greater detail in U.S. patent application Ser. No. 13/595,438, titled "Multiple Table Tokenization", filed Aug. 27, 2012, the contents of which are hereby incorporated by reference.

Centralized Tokenization Environment Overview

Figure 1:
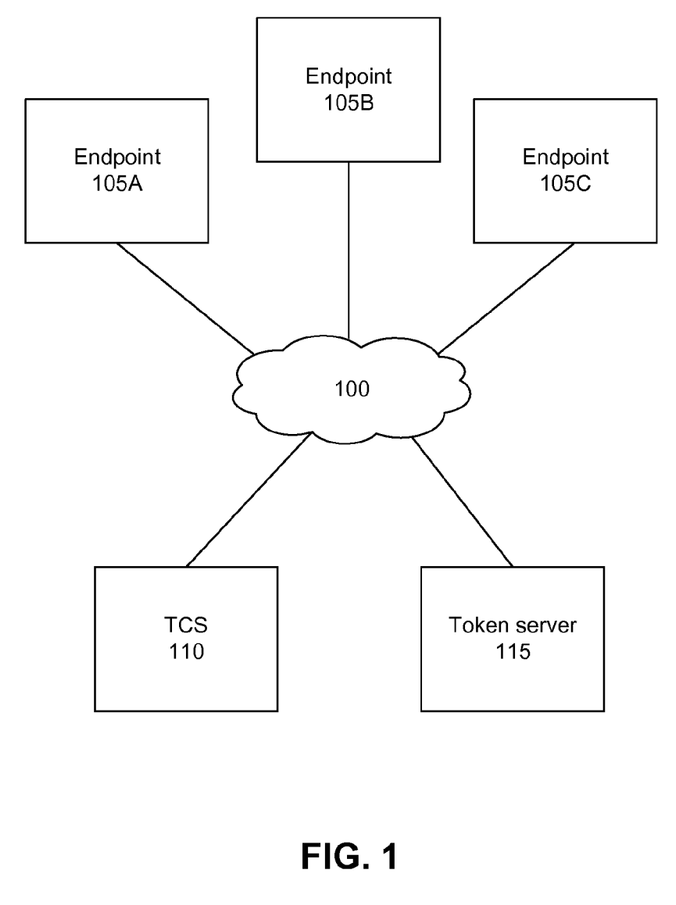
FIG. 1 illustrates an example centralized tokenization environment, according to one embodiment.

FIG. 1 illustrates an example centralized tokenization environment, according to one embodiment. The environment of FIG. 1 includes a plurality of endpoints 105a, 105b, and 105c (referred to individually and collectively as "endpoint 105" herein), a TCS 110, and a token server 115. The entities of FIG. 1 are, include, or are implemented within computing devices and configured to transmit and receive data through a connecting networking 100. In other embodiments, the tokenization environment illustrated in FIG. 1 can include additional, fewer, or different entities, and the entities illustrated can perform functionalities differently or other than those described herein. Further, any number of each type of entity shown in FIG. 1 can be included in various embodiments of a tokenization environment. For example, thousands or millions of endpoints can communicate with one or more TCS and/or token server.

The connecting network 100 is typically the Internet, but may be any network, including but not limited to a LAN, a MAN, a WAN, a mobile wired or wireless network, a private network, a virtual private network, a direct communication line, and the like. The connecting network can be a combination of multiple different networks. In addition, the connecting network 100 can be located within any entity illustrated in FIG. 1 in whole or in part, and can include both inner- and inter-entity communication lines.

An endpoint 105 is a computing device, and can be a mobile device such as a mobile phone, a tablet computer, or a laptop computer. An endpoint can also be a traditionally non-mobile entity, such as a desktop computer, a television, an ATM terminal, a ticket dispenser, a retail store payment system, a website, a database, and the like. Each endpoint includes software configured to allow a user of the endpoint to interact with other entities within the environment of FIG. 1. For example, the endpoint can include a mobile wallet application or other payment application configured to allow a user to use the endpoint to transmit payment information when conducting a transaction, for instance at a store or restaurant. In such an example, the endpoint can request and receive token certificates from the centralized TCS 110 and tokens from the token server 115 for use in tokenizing the payment information prior to transmission.

The TCS 110 is configured to store and provide token certificates associated with tokens used by endpoints 105 in tokenizing and detokenizing data. The token server 115 is configured to generate and/or retrieve tokens, and to provide the generated or retrieved tokens to an endpoint 105 for use in tokenizing and detokenizing data. Both the TCS and the token server are computing devices configured to perform the functionalities described herein. The TCS and the token server are described below in greater detail.

Figure 2:
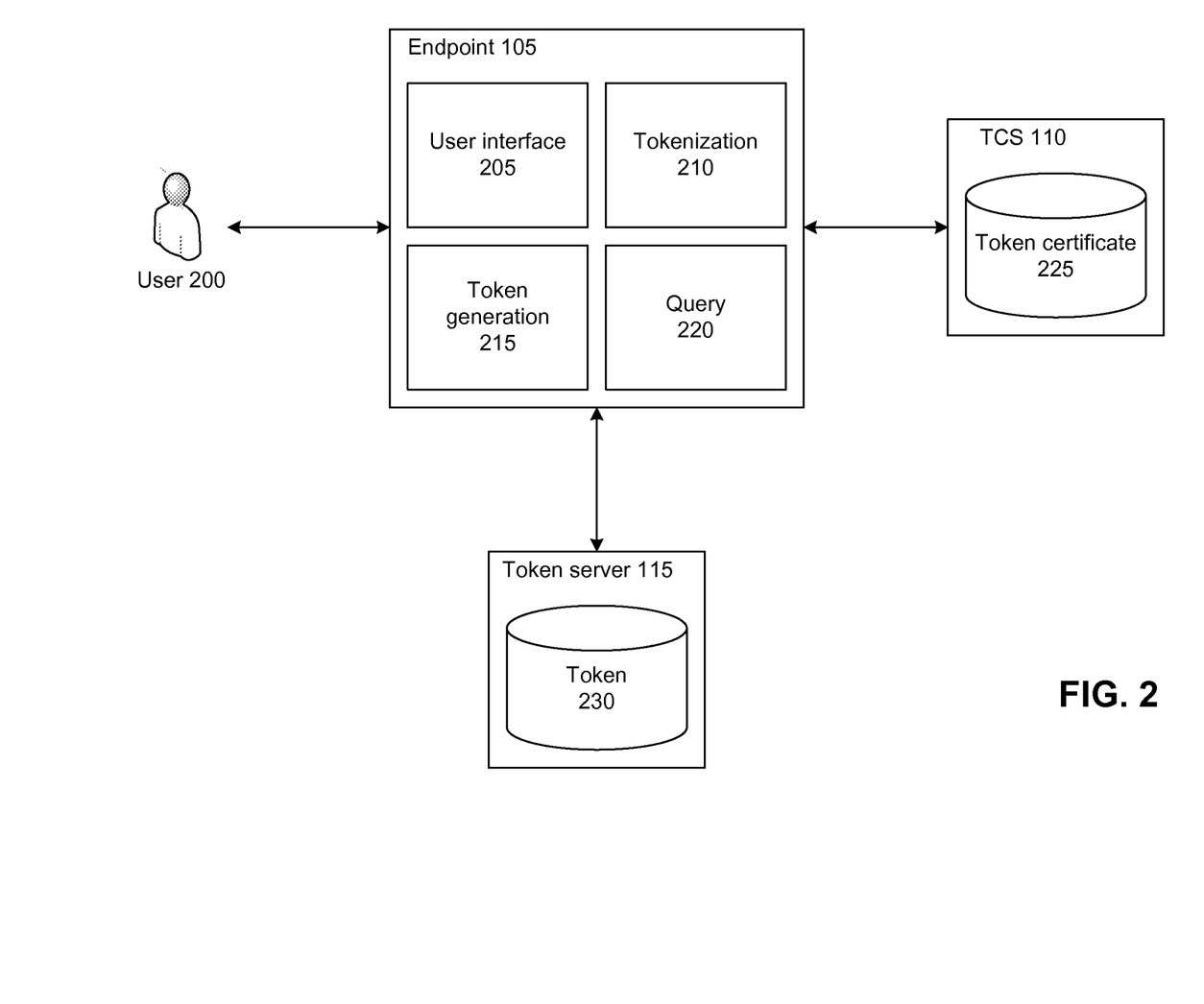
FIG. 2 illustrates components of the centralized tokenization environment of FIG. 1, according to one embodiment.

FIG. 2 illustrates components of the centralized tokenization environment of FIG. 1, according to one embodiment. A user 200 uses an endpoint 105 to tokenize data, such as sensitive financial data, credit card data, password or verification information, and the like. The endpoint includes a user interface 205, a tokenization module 210, a token generation module 215, and a query module 220. The endpoint is communicatively coupled to the TCS 110, which includes a token certificate storage module 225. The endpoint is also communicatively coupled to the token server 115, which includes a token storage module 230. It should be noted that in other embodiments, the entities of FIG. 2 can include different or additional module configured to perform the functionalities described herein.

The user interface module 205 presents an interface configured to allow the user 200 to interact with the endpoint 105. The user interface module can present an interface via a display associated with the endpoint, and can receive user inputs via one or more input mechanisms associated with the endpoint. In an example embodiment in which the endpoint is a mobile phone, the user interface module can display one or more screens associated with a banking application running on the mobile phone on the mobile phone's display, and can receive a selection of a transaction to perform via the mobile phone's touch-screen capabilities. In an example embodiment in which the endpoint is a mass transit ticket dispenser, the user interface module can display an interface on a ticket dispenser display prompting the user to select a ticket option via a keyboard or keypad input mechanism.

For the sake of simplicity, the remainder of the description herein will be limited to embodiments in which the user 200 uses the endpoint 105 to perform a transaction. As used herein, "transaction" refers to the exchange of funds for goods or services. During a transaction, the endpoint provides sensitive data to or receives sensitive data from a participating entity (such as another endpoint, a bank, a store, and the like). Sensitive data can include but is not limited to: credit card numbers, debit card numbers, bank account numbers, PIN numbers, gift card numbers, ticket and other pay-card information (such as identifying information, or account balance information), identity information, or any other information used to conduct transactions. Accordingly, during transactions, the endpoint tokenizes all or part of the sensitive data associated with the transaction. It should be emphasized that in other embodiments, the principles associated with the tokenization of sensitive data using token certificates described herein apply equally to non-financial interactions and non-financial sensitive data.

The tokenization module 210 is configured to tokenize all or part of the sensitive data associated with a transaction requested by the user 200. In one embodiment, the sensitive data is received from the user via the user interface module 205 in conjunction with a received transaction request. For example, a user can request a purchase via the endpoint 105, and can enter credit card information at the endpoint in order to complete the purchase. In other embodiments, the sensitive data is stored at the endpoint or at another entity, and is retrieved by the tokenization module in response to a transaction request received from the user via the user interface module. For example, a user can request a purchase via the endpoint, and can select credit card information stored at the endpoint to complete the purchase.

The tokenization module 210 can tokenize all or part of the sensitive data associated with a requested transaction according to one or more tokenization parameters. The tokenization parameters can be selected by the user 200, can be default tokenization parameters, can be based on the type of transaction being performed, can be based on the time and date of the requested transaction, or can be based on any other factor associated with the requested transaction. The tokenization parameters identify a portion of the sensitive data to be tokenized, and identify one or more tokens for use in tokenizing the sensitive data. It should be noted that the portion of the sensitive data to be tokenized and the tokens to be used in the tokenization can instead be selected by a user, can be based on the type of transaction being used, or can be randomly selected, though these embodiments will not be discussed further herein for the purposes of simplicity.

The tokenization module 210 accesses one or more tokens identified by the tokenization parameters for use in tokenizing the sensitive data. The tokens can be pre-generated and stored at the endpoint 105 in a token storage module (not illustrated in the embodiment of FIG. 2). The tokens can also be pre-generated and stored at the token server 115 in the token storage module 230, and can be requested by the tokenization module prior to tokenizing the sensitive data. In some embodiments, the identified tokens are generated by the token generation module 215, for instance in response to the transaction requested by the user 200. In such embodiments, the generated tokens can be stored at the endpoint, or can be transmitted to the token server for storage and subsequent provision to a detokenizing entity. It should be emphasized that although reference is made to individual tokens herein, the tokenization module can identify one or more token tables (such as SLTs) including a plurality of tokens for use in tokenizing sensitive data. In such embodiments, the tokenization module can select particular tokens within the identified token tables for use in tokenizing the sensitive data based on, for example, characteristics of the sensitive data, the identity of the requesting user, the tokenization parameters used by the tokenization module, the type of requested transaction, or any other suitable transaction parameter.

Upon identifying one or more tokens for use in tokenizing sensitive data, the tokenization module 210 accesses token certificates associated with the identified tokens. As used herein, "token certificate" refers to a set of information associated with a particular token. A token certificate can include information related to the generation or use of a token by the endpoint 105 and by any other endpoints that have used the token. For instance, a token certificate can include the time and date that a token was generated, each time and date that the token was requested or used, the identity of any user or endpoint that requests the token, the identity of the source of the sensitive data to be tokenized, a count representing the number of times the token has been used to tokenize data, and the like.

Each token certificate can also include the status of the token associated with the token certificate. For instance, a token certificate can indicate that the token is available for use in tokenization/detokenization ("available"), that the token is already in use by another endpoint or entity and is not available ("checked out"), or that the security of the token has been compromised or that the token itself has been maliciously altered ("revoked"). Each token certificate can also include one or more use rules specifying the permitted use of the token associated with the token certificate. Use rules included in each token certificate can restrict token use based on the identity of the user 200, use based on characteristics of the endpoint 105, use based on a particular time or date of the requested transaction, use associated with a transaction type, and the like.

In one embodiment, the tokenization module accesses token certificates via the query module 220. The query module 220 is configured to query token certificates associated with the identified tokens from the TCS 110. The query module can identify the requested token certificates by providing the identified tokens themselves to the TCS, or by providing one or more token identifiers identifying the one or more tokens to the TCS.

The TCS 110, in response to receiving a query for token certificates from the query module 220, retrieves the requested token certificates from the token certificate storage module 225. The TCS then provides the retrieved token certificates to the query module, which in turn provides the retrieved token certificates to the tokenization module 210. It should be noted that instead of providing the retrieved token certificates to the query module, the TCS may instead provide various information included within the token certificate. For example, the TCS may retrieve a requested token certificate, and may provide the token status or permitted use included within the token certificate. In such an example, if the query module requests a token certificate associated with an identified token for use in tokenizing sensitive data, the TCS can determine that the status of the token associated with the retrieved token certificate is "revoked", and can inform the query module that the identified token has been revoked and should not be used in tokenization (as opposed to providing the token certificate itself to the query module). In the event that a requested token certificate is not stored by the TCS, the TCS can inform the query module that the requested token certificate is not stored at the TCS.

The TCS 110, in response to receiving a query for a token certificate from an endpoint 105 for an identified token, and responsive to the token certificate indicating that the token status is "available", can update the token certificate to indicate that the token status is "checked out". When the endpoint completes the tokenization operation being performed with the identified token, the token certificate can be updated to indicate that the token status is again "available". This informs other endpoints that query the TCS for the token certificate during the use of the token by the first endpoint that the token is currently in use without directly communicating with the first endpoint, preventing token collisions between endpoints.

The tokenization module 210, in response to accessing the one or more identified tokens and querying the TCS 110 for token certificates associated with the one or more identified tokens, tokenizes the sensitive data associated with the requested transaction using the accessed tokens and subject to the queried token certificates. For example, if the token certificates specify that the identified tokens are available, the tokenization module tokenizes the sensitive data using the accessed tokens, according to the tokenization parameters associated with the requested transaction. The tokenized sensitive data can stored, for instance at the endpoint 105, for subsequent retrieval, or can be transmitted to another entity involved in the transaction.

In the event that the queried token certificates indicate that an identified token has been checked out, the tokenization module 210 can identify and retrieve an alternative token for use in tokenizing the sensitive data. Likewise, in the event that the queried token certificates indicate that an identified token has been "revoked", the tokenization module can identify and retrieve an alternative token. By using token certificates stored by a central TCS 110 configured to receive requests for token certificates from a plurality of endpoints 105 in a tokenization environment, the centralized control of tokens can be enabled. For example, if it is determined that the security of a particular token or token table has been compromised, the token certificate associated with the token or token table can be updated to reflect such a security compromise (by changing the status of the token to "revoked"), and the use of the token or token table can be prevented across the entire tokenization environment.

In addition, if the transaction does not satisfy one or more use rules included in the token certificate associated with an identified token, the tokenization module 210 can identify and retrieve an alternative token for use in tokenizing the sensitive data. For example, if a use rule limits the use of an identified token to transactions associated with a particular bank or to weekend transactions, and if the transaction fails to satisfy these requirements, the tokenization module can identify an alternative token for use in the requested transaction.

The tokenization module can also tokenize sensitive data according to one or more tokenization parameters that restrict the use of tokens that have been used within a threshold amount of time, or that have been used over a threshold number of times. For example, a tokenization parameter may restrict the use of tokens in tokenizing sensitive data to tokens that have not been used in the previous 12 hours. In such an example, the tokenization module can request a tokenization certificate associated with an identified token, can determine a time the token was last used according to the token certificate, and can allow or prevent the use of the token based on the determined time. In another example, a tokenization parameter may restrict the use of tokens in tokenizing sensitive data to tokens that have been used to tokenize sensitive data less than 10 times in 24 hours. In such an example, the tokenization module can request a tokenization certificate associated with an identified token, can determine a number of times the token has been used, and can allow or prevent the use of the token based on the determined number of token uses.

As described above, if the tokenization module 210 determines that an identified token cannot be used in a tokenization operation (for instance, the status included in a token certificate associated with the token is "checked out" or "revoked", one or more use rules included in the token certificate are not satisfied, and/or one or more tokenization parameters are not satisfied by information included in the token certificate, an alternative token is identified for use in the tokenization operation. It should be noted, however, that the tokenization module can instead deny the requested transaction in response to a determination that an identified token cannot be used in a tokenization operation. In such embodiments, the endpoint 105 can display a tokenization error to the user 200 including, for example, the reason for the detokenization error (such as the revocation of a token). The endpoint can also prompt the user to attempt the transaction again, to perform the transaction by alternative means, or to remedy any errors that caused the tokenization module to deny the requested transaction.

Upon tokenizing sensitive data, the tokenization module 210 updates the queried token certificates associated with the tokens used in the tokenization of the sensitive data to reflect that the tokens were used in the tokenization operation. For example, the tokenization module can change the status of a token used in tokenization to "checked out" to prevent the token from being used in subsequent tokenization operations until the sensitive data is detokenized using the token. Such an example allows the use of tokens to be restricted such that no one token is used to tokenize sensitive data for two simultaneous or concurrent tokenizing and detokenization operations.

The tokenization module 210 can also update a queried token certificate to include a time and/or date of tokenizing sensitive data using an associated token, to increment a stored count representing the number of times the associated token has been used, and the like. In one embodiment, the tokenization module updates the token certificate, and the query module 220 transmits the updated token certificate back to the TCS 110 for storage in the token certificate storage module 225. Alternatively, in embodiments in which the TCS provides token certificate information in response to token certificate queries (as opposed to providing the token certificate itself), the query module can instead provide to the TCS characteristics of the transaction (such as a time and date of tokenization using an associated token), can request a change in status of an associated token (for instance, from available to checked out), and the like. In response to receiving such provided transaction characteristics and/or status change requests, the TCS can update a token certificate stored in the token certificate storage module associated with a token used in tokenizing sensitive data to include the transaction characteristics and requested status change.

In embodiments in which the TCS 110 receives a query for a token certificate that is not stored in the token certificate storage module 225, the TCS can indicate to the query module 220 that the queried token certificate is not stored at the TCS. In response, the tokenization module 210 can tokenize sensitive data using an identified token, and can generate a token certificate for subsequent transmission to and storage at the TCS by the query module. Alternatively, the query module can provide characteristics of the transaction to the TCS, and the TCS can generate and store a token certificate associated with the token used in the tokenization operation.

The tokenization module 210 can also detokenize previously tokenized sensitive data according to various tokenization parameters. For example, the endpoint 105 can be a mobile phone used by the user 200 (for instance, a seller) to receive tokenized payment information from another mobile phone associated with a second user (for instance, a buyer). In such embodiments, the tokenization module identifies one or more tokens used to tokenize the received tokenized sensitive data. The tokenization module queries token certificates associated with the identified tokens, for instance via the query module 220. If the TCS 110 stores a queried token certificate, the requested token certificate is provided to the endpoint, and the tokenization module detokenizes the tokenized sensitive data based, in part, on the status of the token or any use rules included in the queried token certificate. For example, the tokenization module may only detokenize the tokenized sensitive data with a token if the status of the token in the associated token certificate is "checked out" (indicating that the token is being reserved for the endpoint to detokenize previously tokenized data), or if the identity of the user requesting the transaction associated with the detokenization operation satisfies a use rule included in the token certificate restricting token use to certain users.

The tokenization module 210 can update queried token certificates based on the detokenization of sensitive data using one or more tokens associated with the queried token certificates. For example, if a token certificate associated with a token used in detokenization indicates the status of the token is "checked out" prior to the detokenization operation, the tokenization module can update the status of the token in the queried token certificate to "available" after the detokenization. The tokenization module can also update token certificates with a time and/or date of a detokenization operation, characteristics of the detokenization operation, and the like. In embodiments in which the TCS 110 does not store a queried token certificate, the tokenization module can access an identified token, can detokenize the tokenized sensitive data, and can generate a token certificate for storage by the TCS. Alternatively, the TCS can generate and store a token certificate for a token used by the tokenization module to detokenize sensitive data.

The tokenization module 210 can be configured to tokenize and detokenize sensitive data with one or more identified tokens in a requested transaction prior to querying the TCS 110 for token certificates associated with the identified tokens (referred to herein as operating in "fast mode"). In such embodiments, after tokenizing or detokenizing sensitive data using the identified tokens, the query module 220 subsequently queries the TCS for token certificates associated with the identified tokens. If the TCS stores the queried certificates, the TCS can provide the token certificates to the query module for updating to reflect the use of the identified tokens in the requested transaction. Alternatively, the query module can inform the TCS of the use of the identified tokens, and the TCS can update the token certificates associated with the identified tokens accordingly. In embodiments in which the TCS does not store token certificates associated with the identified tokens, the query module or the TCS can create the token certificates reflecting the use of the identified tokens in the requested transaction for subsequent storage. Operating in fast mode can potentially increase the performance of the tokenization module specifically and the endpoint 105 generally, though it is possible that checked out or revoked tokens can be used in tokenization/detokenization operations and that collisions can occur between endpoints requesting the same token.

Tokenization in a Centralized Tokenization Environment

By utilizing a central TCS 110, tokenization in the centralized tokenization environments of FIGS. 1 and 2 allow for the tracking, management, and control of token use between a plurality of endpoints 105. A token certificate associated with a given token and stored in the TCS allows endpoints to independently verify the number of times the token has been used, the last time the token has been used, and the status of the token, without requiring the endpoints to directly communicate with each other. For instance, if a tokenization policy implemented within a centralized tokenization environment only allows a given token to be used ten times a day, each individual endpoint in the centralized tokenization environment can verify whether or not the use threshold for the token has been exceeded for a given day by querying the TCS for the token certificate associated with the token prior to using the token. Similarly, if a tokenization policy restricts each token from being used more than once per hour, each endpoint can verify whether or not a token has been used in the previous hour by querying the TCS for the token certificate associated with the token.

The central TCS 110 also allows endpoints 105 to individually determine if a token's security has been compromised by updating the token certificate associated with the token to indicate a revoked token status. This allows a first endpoint to inform all other endpoints of the security compromise and to prevent future use of the token without requiring the first endpoint to communicate directly with any other endpoint.

The central TCS 110 also allows for the prevention of collisions between endpoints 105 within the centralized tokenization environment. As used herein, "collision" refers to the concurrent use of a token by different endpoints. It may be desirable to avoid collisions, particularly in embodiments where a tokenization policy implemented within the centralized tokenization environment restricts the use of individual tokens.

For example, assume that a tokenization policy limits the use of a given token to a threshold of four uses per hour, and that the token has already been used three times in a particular hour. If, during this hour, both a first and a second endpoint use the token without directly communicating, the total number of times that the token has been used during the hour (five) will exceed the policy threshold (four). Thus, to remedy collisions, a first endpoint to use a particular token can update the token certificate associated with the token to change the token status to "checked out". When a second endpoint attempts to use the token, the second endpoint will query the TCS, will determine that the token is currently checked out, and will not use the token in response, avoiding a potential collision. When the first endpoint finishes a tokenization operation, or when an associated endpoint performs a counterpart detokenization operation using the same token, the token certificate can be updated again to change the token status from "checked out" to "available".

The central TCS 110 can also allow for external monitoring and auditing of token use. Token certificates stored by the TCS are updated by endpoints 105 each time the respective tokens are used to reflect details of the transactions involved in their usage. Accordingly, by querying the TCS for a token certificate associated with a particular token, details of the token's use can be obtained and analyzed. This allows for an external determination of whether a token has been used in a suspicious or malicious manner, and can allow an external entity to revoke a token in response to a detected security breach. Similarly, querying the TCS for token certificates allows an external entity to monitor the usage of particular tokens by a particular endpoint. If it is determined that a particular endpoint is using one or more tokens in a manner indicative of a security breach, the token certificates associated with the one or more tokens can be updated with use rules preventing the use of the tokens by the endpoint.

As described above, although operating in "fast mode" can result in collisions between endpoints 105 for particular tokens, which in turn can result in violations of a tokenization policy implemented within a tokenization environment, the maintenance of token certificates for tokens used in "fast mode" tokenization operations still allows for subsequent auditing of the token certificates. In addition, by tokenizing and/or detokenizing sensitive information without waiting for a query of the TCS 110 allows endpoints to avoid potential communication bottlenecks between the endpoints and the TCS. For instance, if a large number of endpoints simultaneously requests token certificates from the TCS, the TCS may be slower to retrieve queried token certificates, and communications with the TCS may be delayed due to bandwidth limitations. Thus, by operating in fast mode, an endpoint can perform a tokenization operation and avoid such bottlenecks.

Figure 3A:
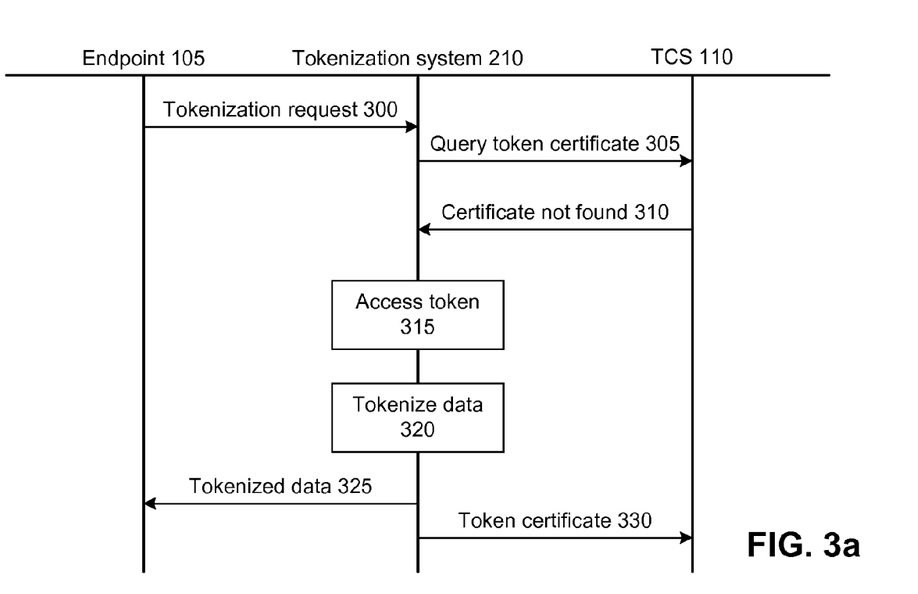
FIGS. 3a and 3b are flow diagrams illustrating the tokenization of data in a centralized tokenization environment, according to one embodiment.
Figure 3B:
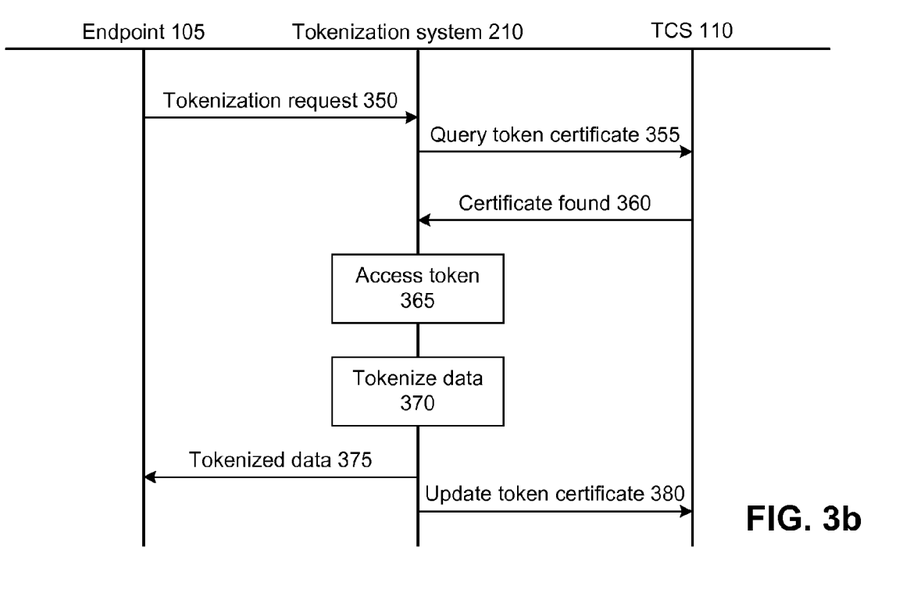

FIGS. 3a and 3b are flow diagrams illustrating the tokenization of data in a centralized tokenization environment, according to one embodiment. In the embodiment of FIG. 3a, an endpoint 105 requests 300 a tokenization operation from the tokenization system 210, for instance in response to a transaction requested by a user of the endpoint. The tokenization request can originate from, for example, a payment application running on the endpoint to tokenize sensitive data.

In response to receiving the tokenization request, the tokenization system 210 queries 305 a TCS 110 for a token certificate. The token certificate query is directed to a token certificate associated with a token identified for use in tokenizing the sensitive data. As noted above, the token can be identified according to one or more tokenization parameters implemented by the tokenization system, based on the identity of the endpoint 105 or a user of the endpoint, based on characteristics of the requested transaction, and the like. It should be emphasized that although reference is made in the embodiments of FIGS. 3a-3b, 4a-4c, and 5a-5b to a single token and associated tokenization certificate, in practice a tokenization operation as described herein can include a plurality of tokens and associated token certificates.

In the embodiment of FIG. 3a, the TCS 110 indicates 310 to the tokenization system 210 that a token certificate associated with a token identified for use in the requested tokenization operation is not stored at the TCS. In response, the tokenization system accesses 315 the identified token, and tokenizes 320 sensitive data associated with the requested tokenization operation using the accessed token. Accessing the identified token can include retrieving a pre-generated token stored at the tokenization system or elsewhere (such as a token server), or can include generating the identified token. The sensitive data associated with the requested tokenization operation can be tokenized according to a set of tokenization parameters associated with or selected by the tokenization system, the endpoint 105, a user of the endpoint, a tokenization policy implemented within the tokenization environment of FIG. 3a, or based on any other factor associated with the requested tokenization operation.

The tokenized data is provided 325 by the tokenization system 210 to the endpoint 105. In addition, a token certificate associated with the token used in the tokenization operation is provided 330 by the tokenization system to the TCS 110 for storage. In one embodiment, the tokenization system generates the token certificate based on characteristics of the tokenization operation performed by the tokenization system, and provides the generated token certificate to the TCS. Alternatively, the tokenization system can provide information associated with the tokenization operation to the TCS, and the TCS can generate the token certificate based on the received tokenization operation information.

In the embodiment of FIG. 3b, the endpoint 105 requests 350 a tokenization operation from the tokenization system 210, and the tokenization system in turn queries 355 the TCS 110 for a token certificate associated with a token identified for use in the requested tokenization operation. The TCS indicates 360 to the tokenization system that the TCS stores a token certificate associated with the identified token. The TCS can provide the token certificate to the tokenization system, or can provide token information included within the token certificate (such as a status of the identified token) to the tokenization system.

The tokenization system 210 then accesses 365 the identified token and tokenizes 370 the sensitive data using the retrieved token based on the token certificate stored by the TCS 110. For example, the tokenization system may only tokenize the sensitive data if the token status included within the token certificate is "available" (and not "checked out" or "revoked"), if one or more use rules included within the token certificate are satisfied by characteristics of the requested tokenization operation, if one or more tokenization parameters implemented by the tokenization system are satisfied by information included within the token certificate, and the like. If one or more of these conditions are not satisfied, the tokenization system can deny the requested tokenization operation, or can identify an alternative token for use in the requested tokenization operation.

The tokenized data is provided 375 by the tokenization system 210 to the endpoint 105. In addition, the token certificate associated with the accessed token is updated 380 and provided to the TCS 110. As described above, either the tokenization system or the TCS can update the token certificate for storage by the TCS. Further, as described above, the token certificate can be updated to, for example, change the status of the accessed token to "checked out", or to included the details of the tokenization operation (such as the time and data of operation, the identity of the endpoint or the user of the endpoint, and the like).

Figure 4A:
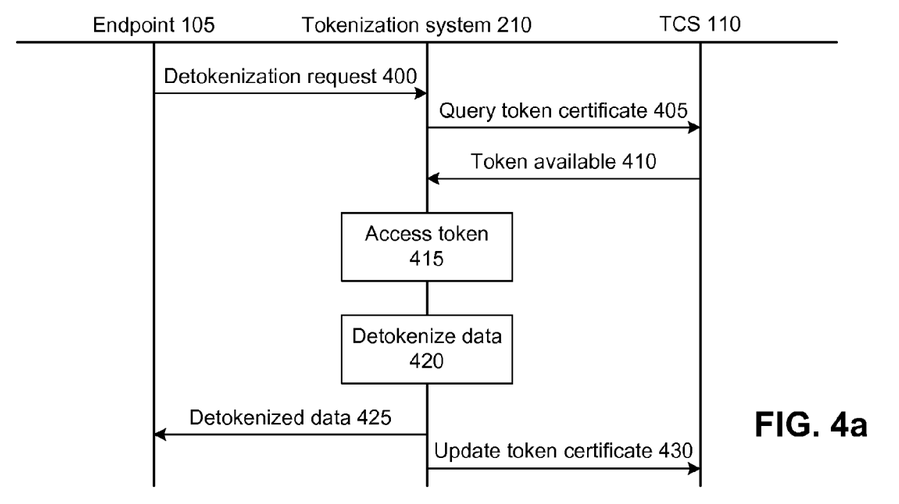
FIGS. 4a, 4b, and 4c are flow diagrams illustrating the detokenization of data in a centralized tokenization environment, according to one embodiment.
Figure 4B:
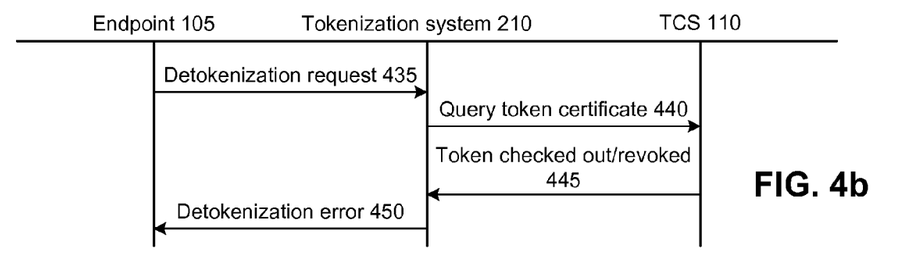
Figure 4C:
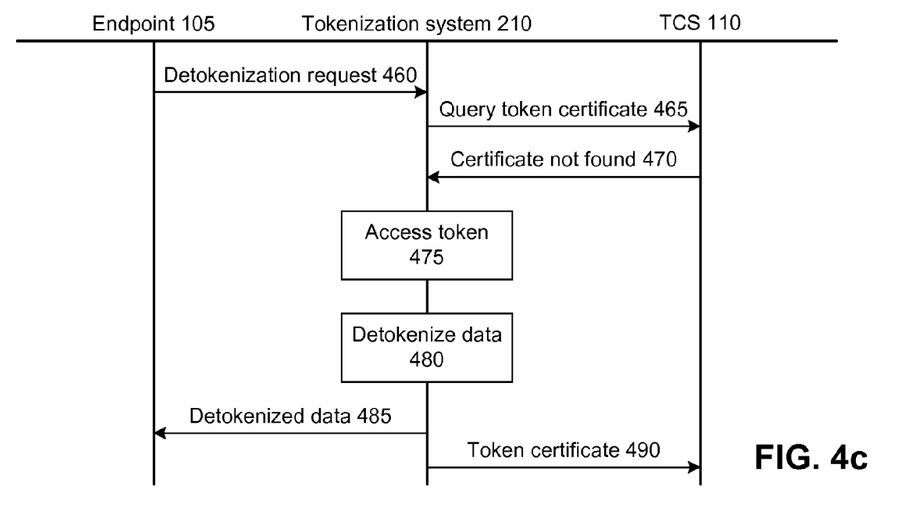

FIGS. 4a, 4b, and 4c are flow diagrams illustrating the detokenization of data in a centralized tokenization environment, according to one embodiment. In the embodiment of FIG. 4a, an endpoint 105 requests 400 a detokenization operation from the tokenization system 210 to detokenize previously tokenized sensitive data, for instance in response to a transaction requested by a user of the endpoint. As with the tokenization request described above, the detokenization request can originate from an application running on the endpoint to detokenize sensitive data received by the application.

The tokenization system 210, in response the request 400, queries 405 the TCS 110 for a token certificate associated with a token identified by the tokenization system for use in the requested detokenization operation. In the embodiment of FIG. 4a, the TCS informs 410 the tokenization system that the status of the identified token included within the queried token certificate is "available". In response, the tokenization system accesses 415 the identified token, and detokenizes 420 the tokenized data. The detokenized data is provided 425 to the endpoint 105, and the token certificate associated with the accessed token is updated 430 to include the details of the detokenization operation and/or to change the status of the accessed token to, for example, "available".

In the embodiment of FIG. 4b, the tokenization system 210 receives 435 the detokenization request from the endpoint 105, and queries 440 the TCS 110 for a token certificate associated with a token identified for use in the requested detokenization. The TCS informs 445 the tokenization system that the queried token certificate indicates that the identified token is checked out or revoked, and the tokenization system provides 450 a detokenization error to the endpoint, denying the detokenization request. As described above, the tokenization system can inform the endpoint of the reasons for the detokenization error, and can prompt a user of the endpoint to correct the error.

In the embodiment of FIG. 4c, the tokenization system 210 receives 460 the detokenization request from the endpoint 105, and queries 465 the TCS 110 for a token certificate associated with a token identified for use in the requested detokenization. The TCS informs 470 the tokenization system that the TCS does not store the requested token certificate. In response, the tokenization system accesses 475 the identified token (for instance, by retrieving it from a token server or by generating it), detokenizes 480 the tokenized sensitive information associated with the detokenization request, and provides 485 the detokenized data to the endpoint. The tokenization system provides 490 a token certificate associated with the accessed token to the TCS for storage, or provides information associated with the detokenization operation to the TCS for inclusion in a generated token certificate.

Figure 5A:
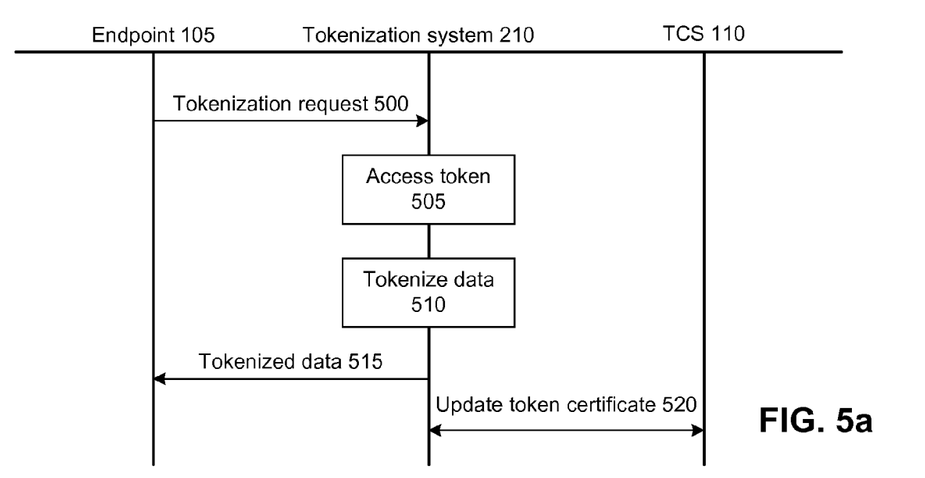
FIGS. 5a and 5b are flow diagrams illustrating the tokenization and detokenization of data in a centralized tokenized environment, according to one embodiment.

FIGS. 5a and 5b are flow diagrams illustrating the tokenization and detokenization of data in a centralized tokenized environment, according to one embodiment. In the embodiment of FIG. 5a, the tokenization system 210 receives 500 a tokenization request from an endpoint 105. In response, the tokenization system identifies a token for use in the requested tokenization, accesses 505 the identified token, and tokenizes 510 sensitive data associated with the requested tokenization using the accessed token. The tokenization system provides 515 the tokenized data to the endpoint, and subsequently queries a TCS 110 for a token certificate associated with the accessed token. If the TCS includes a token certificate associated with the accessed token, the token certificate is updated 520 to reflect the tokenization operation. If the TCS does not include a token certificate associated with the accessed token, a token certificate is generated including details of the tokenization operation.

Figure 5B:
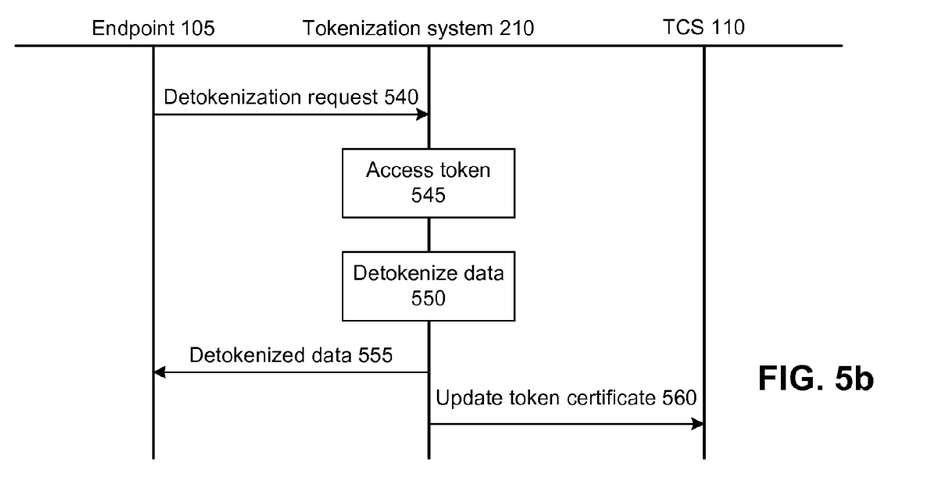

In the embodiment of FIG. 5b, the tokenization system 210 receives 540 a detokenization request from an endpoint 105. In response, the tokenization system identifies a token for use in the requested detokenization, accesses 545 the identified token, and detokenizes 550 previously tokenized sensitive information associated with the requested detokenization using the accessed token. The tokenization system provides 555 the detokenized data to the endpoint, and queries the TCS 110 for a token certificate associated with the accessed token. If the TCS includes a token certificate associated with the accessed token, the token certificate is updated 560 to reflect the detokenization operation. If the TCS does not include a token certificate associated with accessed token, a token certificate is generated including details of the detokenization operation.

Additional Considerations

The present invention has been described in particular detail with respect to one possible embodiment. Those of skill in the art will appreciate that the invention may be practiced in other embodiments. First, the particular naming of the components and variables, capitalization of terms, the attributes, data structures, or any other programming or structural aspect is not mandatory or significant, and the mechanisms that implement the invention or its features may have different names, formats, or protocols. Also, the particular division of functionality between the various system components described herein is merely exemplary, and not mandatory; functions performed by a single system component may instead be performed by multiple components, and functions performed by multiple components may instead performed by a single component.

Some portions of above description present the features of the present invention in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality.

Unless specifically stated otherwise as apparent from the above discussion, it is appreciated that throughout the description, discussions utilizing terms such as "determine" refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by real time network operating systems.

The present invention also relates to an apparatus for performing the operations herein. This apparatus may be specially constructed for the required purposes, or it may comprise a general-purpose computer selectively activated or reconfigured by a computer program stored on a non-transitory computer readable medium that can be accessed by the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of computer-readable storage medium suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will be apparent to those of skill in the art, along with equivalent variations. In addition, the present invention is not described with reference to any particular programming language. It is appreciated that a variety of programming languages may be used to implement the teachings of the present invention as described herein, and any references to specific languages are provided for invention of enablement and best mode of the present invention.

The present invention is well suited to a wide variety of computer network systems over numerous topologies. Within this field, the configuration and management of large networks comprise storage devices and computers that are communicatively coupled to dissimilar computers and storage devices over a network, such as the Internet.

Finally, it should be noted that the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

What is claimed is:

1. A method for tokenizing data, comprising:
   receiving a request to tokenize sensitive data;
   identifying a token for use in tokenizing the sensitive data based on a value of a portion of the sensitive data, the identified token comprising a token value mapped to the value of the portion of the sensitive data by a token table mapping each of a plurality of input values to a different token value before the request to tokenize sensitive data is received;
   querying a token certificate store for a token certificate associated with the identified token, each token certificate stored by the token certificate store comprising a status of an associated token;
   responsive to a determination that the token certificate store does not store a token certificate associated with the identified token:
      tokenizing the sensitive data with the identified token by replacing the portion of the sensitive data with the token value;
      generating a token certificate associated with the identified token based on the tokenization of the sensitive data with the identified token; and
      providing the generated token certificate to the token certificate store for storage.

2. The method of claim 1, further comprising:
   responsive to a determination that the token certificate store contains the token certificate associated with the identified token:
      tokenizing the sensitive data with the identified token by replacing the portion of the sensitive data with the token value; and
      updating the token certificate associated with the identified token based on the tokenization of the sensitive data for storage in the token certificate store.

3. The method of claim 2, wherein tokenizing the sensitive data with the identified token comprises:
   accessing the status of the identified token from the token certificate associated with the identified token; and
   tokenizing the sensitive data with the identified token responsive to the accessed status indicating that the identified token is available.

4. The method of claim 3, further comprising:
   rejecting the tokenization request responsive to the accessed status indicating that the identified token is checked out or revoked.

5. The method of claim 4, further comprising:
   responsive to rejecting the tokenization request:
      identifying a second token for use in tokenizing the sensitive data;
      querying the token certificate store for a second token certificate associated with the second identified token; and
      responsive to a determination that the token certificate store contains the second token certificate:
         tokenizing the sensitive data with the second identified token; and
         updating the second token certificate based on the tokenization of the sensitive data for storage in the token certificate store.

6. The method of claim 5, further comprising:
   responsive to a determination that the token certificate store does not contain the second token certificate:
      tokenizing the sensitive data with the identified second token;
      generating the second token certificate based on the tokenization of the sensitive data with the identified second token; and
      providing the generated second token certificate to the token certificate store for storage.

7. The method of claim 1, wherein the generated token certificate associated with the identified token further comprises a use rule describing a permitted use of the identified token based on characteristics of the tokenization request.

8. The method of claim 7, wherein tokenizing the sensitive data with the identified token further comprises:
tokenizing the sensitive data with the identified token subject to characteristics of the tokenization request satisfying the use rule.

9. The method of claim 1, further comprising:
tokenizing the sensitive data with the identified token prior to querying the token certificate store for the token certificate associated with the identified token.

10. The method of claim 1, wherein the tokenization request is received at an endpoint, and further comprising:
transmitting the tokenized data to a second endpoint for storage.

11. The method of claim 1, wherein the portion of the sensitive data comprises less than all of the sensitive data.

12. A system for tokenizing data, comprising:
an endpoint comprising one or more hardware processors
a non-transitory computer-readable storage medium storing executable computer instructions configured to, when executed by the one or more hardware processors:
receive a request to tokenize sensitive data;
identify a token for use in tokenizing the sensitive data based on a value of a portion of the sensitive data, the identified token comprising a token value mapped to the value of the portion of the sensitive data by a token table mapping each of a plurality of input values to a different token value before the request to tokenize sensitive data is received;
query a token certificate store for a token certificate associated with the identified token, each token certificate stored by the token certificate store comprising a status of an associated token;
responsive to a determination that the token certificate store does not store a token certificate associated with the identified token:
tokenize the sensitive data with the identified token by replacing the portion of the sensitive data with the token value;
generate a token certificate associated with the identified token based on the tokenization of the sensitive data with the identified token; and
provide the generated token certificate to the token certificate store for storage.

13. The system of claim 12, wherein the endpoint is further configured to:
responsive to a determination that the token certificate store contains the token certificate associated with the identified token:
tokenize the sensitive data with the identified token by replacing the portion of the sensitive data with the token value; and
update the token certificate associated with the identified token based on the tokenization of the sensitive data for storage in the token certificate store.

14. The method of claim 13, wherein tokenizing the sensitive data with the identified token comprises:
accessing the status of the identified token from the token certificate associated with the identified token; and
tokenizing the sensitive data with the identified token responsive to the accessed status indicating that the identified token is available.

15. The system of claim 14, wherein the endpoint is further configured to:
reject the tokenization request responsive to the accessed status indicating that the identified token is checked out or revoked.

16. The system of claim 15, wherein the endpoint is further configured to:
responsive to rejecting the tokenization request:
identify a second token for use in tokenizing the sensitive data;
query the token certificate store for a second token certificate associated with the second identified token; and
responsive to a determination that the token certificate store contains the second token certificate:
tokenize the sensitive data with the second identified token; and
update the second token certificate based on the tokenization of the sensitive data for storage in the token certificate store.

17. The system of claim 16, wherein the endpoint is further configured to:
responsive to a determination that the token certificate store does not contain the second token certificate:
tokenize the sensitive data with the identified second token;
generate the second token certificate based on the tokenization of the sensitive data with the identified second token; and
provide the generated second token certificate to the token certificate store for storage.

18. The system of claim 12, wherein the generated token certificate associated with the identified token further comprises a use rule describing a permitted use of the identified token based on characteristics of the tokenization request.

19. The system of claim 18, wherein tokenizing the sensitive data with the identified token further comprises:
tokenizing the sensitive data with the identified token subject to characteristics of the tokenization request satisfying the use rule.

20. The system of claim 12, wherein the endpoint is further configured to:
tokenize the sensitive data with the identified token prior to querying the token certificate store for the token certificate associated with the identified token.

21. The system of claim 12, further comprising:
the token certificate store, configured to:
in response to receiving a query for a token certificate from the endpoint:
provide the queried token certificate in response to the token certificate being stored by the token certificate store; and
providing an indication that the token certificate store does not store the queried token certificate in response to the token certificate not being stored by the token certificate store;
in response to receiving a generated token certificate from the endpoint:
storing the generated token certificate; and
in response to receiving an updated token certificate from the endpoint:
storing the updated token certificate.

* * * * *

UNITED STATES PATENT AND TRADEMARK OFFICE
CERTIFICATE OF CORRECTION

| | | |
|---|---|---|
| PATENT NO. | : 9,563,788 B2 | |
| APPLICATION NO. | : 14/738830 | |
| DATED | : February 7, 2017 | |
| INVENTOR(S) | : Ulf Mattsson and Yigal Rozenberg | |

It is certified that error appears in the above-identified patent and that said Letters Patent is hereby corrected as shown below:

In the Claims

Claim 12, Column 17, Lines 18-19, delete "an endpoint comprising one or more hardware processors a non-transitory computer-readable storage medium storing" and insert --an endpoint comprising one or more hardware processors and a non-transitory computer-readable storage medium storing--.

Claim 14, Column 17, Lines 57-58, delete "The method of claim 13, wherein tokenizing the sensitive data with the identified token comprises" and insert --The system of claim 13, wherein instructions for tokenizing the sensitive data with the identified token are further configured to:--.

Claim 14, Column 17, Lines 59, delete "accessing the status" and insert --access the status--.

Claim 14, Column 17, Lines 61, delete "tokenizing the sensitive data" and insert --tokenize the sensitive data--.

Signed and Sealed this
Twelfth Day of September, 2017

Joseph Matal
*Performing the Functions and Duties of the*
*Under Secretary of Commerce for Intellectual Property and*
*Director of the United States Patent and Trademark Office*